United States Patent
Johnson (10) Patent No.: US 9,862,531 B2
(45) Date of Patent: Jan. 9, 2018

(54) PIERCING FITMENT ASSEMBLY FOR FLEXIBLE CONTAINER

(71) Applicant: Liqui-Box Corporation, Richmond, VA (US)

(72) Inventor: James W. Johnson, Delaware, OH (US)

(73) Assignee: LIQUI-BOX CORPORATION, Richmond, VA (US)

( * ) Notice: Subject to any disclaimer, the term of this patent is extended or adjusted under 35 U.S.C. 154(b) by 3 days.

(21) Appl. No.: 15/002,577

(22) Filed: Jan. 21, 2016

(65) Prior Publication Data

US 2016/0207684 A1    Jul. 21, 2016

Related U.S. Application Data

(60) Provisional application No. 62/105,806, filed on Jan. 21, 2015.

(51) Int. Cl.
| | |
|---|---|
| *B65D 75/58* | (2006.01) |
| *B65D 5/74* | (2006.01) |
| *B65D 51/22* | (2006.01) |
| *A61M 5/162* | (2006.01) |

(52) U.S. Cl.
CPC ......... *B65D 75/5877* (2013.01); *B65D 5/747* (2013.01); *B65D 51/221* (2013.01); *A61M 5/162* (2013.01)

(58) Field of Classification Search
CPC . A61M 5/162; B65D 51/221; B65D 75/5877; B65D 5/747; B65D 77/064
See application file for complete search history.

(56) References Cited

U.S. PATENT DOCUMENTS

| | | | |
|---|---|---|---|
| 4,325,496 A | 4/1982 | Malpas | |
| 4,813,578 A | 3/1989 | Gordon et al. | |
| 6,378,730 B1 | 4/2002 | Reddy et al. | |
| 6,595,391 B1 * | 7/2003 | Anderson | B65B 55/022 222/105 |

(Continued)

FOREIGN PATENT DOCUMENTS

| | | |
|---|---|---|
| EP | 0402310 A1 | 12/1990 |
| JP | 2008-050054 A | 3/2008 |
| WO | WO 95/22494 A1 | 8/1995 |

*Primary Examiner* — Frederick C Nicolas
*Assistant Examiner* — Bob Zadeh
(74) *Attorney, Agent, or Firm* — Baker & Hostetler LLP (57) ABSTRACT

A piercing fitment assembly for a thin film flexible container containing a liquid having
(A) a spout assembly having a sealing flange sealed to the film of the flexible container and having positioned therein a circular piercing element with at least one piercing point in close proximity to the film of the flexible container;
(B) a threaded plug fitted into the spout assembly and the bottom of the plug being sealed to the film of the flexible container;
(C) a threaded collar positioned in the spout assembly and threadably engaged with the threaded exterior of the threaded plug;
whereby when the threaded collar is moved to engage the threaded plug and the threaded plug is moved away from the film of the flexible container, the film of the flexible container is brought into contact with the piercing end of the piercing element and the film is pierced allowing the liquid from the container to flow out through the spout assembly and out of the flexible container.

8 Claims, 7 Drawing Sheets

(56) References Cited

U.S. PATENT DOCUMENTS

| | | | |
|---|---|---|---|
| 7,980,424 B2 * | 7/2011 | Johnson | B65D 75/5877 |
| | | | 222/105 |
| 2001/0025672 A1 * | 10/2001 | Thibault | A61J 1/2096 |
| | | | 141/329 |
| 2008/0029540 A1 * | 2/2008 | Johnson | B65D 75/5877 |
| | | | 222/83 |
| 2016/0207684 A1 * | 7/2016 | Johnson | B65D 51/221 |
| 2016/0362239 A1 * | 12/2016 | Johnson | B65D 47/2018 |

* cited by examiner

FORM FILL & SEAL ASSEMBLY
PRE-DISPENSE POSITION

PIERCING FITMENT ASSEMBLY FOR FLEXIBLE CONTAINER

CROSS REFERENCE TO RELATED APPLICATIONS

This application claims the benefit of U.S. Provisional Application No. 62/105,806, filed Jan. 21, 2015, of which is incorporated by reference herein in its entirety.

FIELD OF INVENTION

This invention relates to a piercing fitment assembly for use with flexible containers for flowable materials, such as liquids, and including aseptically-packaged flexible containers.

BACKGROUND

Flexible polymeric containers are extensively used throughout the food service industry for storing and dispensing soft drink syrups and other such beverages, as well as wine, dairy products, enteral feeding solutions, fruit juices, tea and coffee concentrates, puddings, cheese sauces, and many other flowable materials, including those that must be filled aseptically. Flexible polymeric containers typically have walls made of polymeric films with either a monolayer or multiple layer structure. The particular polymers constituting the container film layers vary depending on the type of material to be placed in the container. The film layers may also include an oxygen barrier material layer to prevent contact between such materials and oxygen or other gas sensitive contents. The walls of the containers may be metallized, or coated with a metallic layer such as aluminum to prevent incursion of oxygen or other gases.

The flexible polymeric containers may have inlets and/or spouts for filling and dispensing the container contents. The containers are also often placed within a corrugated paper box. Such packaging systems are commonly referred to as "bag-in-box" systems wherein the spout extends through an opening in the box to dispense the contents. Bag-in-box packaging systems are often used in restaurants, institutional food service centers, and convenience stores to facilitate service of liquid food products such as syrups, toppings, condiments, beverages and dairy products. These containers typically have a capacity of 1 to 6 gallons.

Once the container is filled with a desired flowable material, the spout is capped to seal the container and protect the contents from contamination. Depending on the type of contents, the container, spout and cap may be sterilized using steam, hydrogen peroxide (H2O2), radiation or other suitable sterilizing methods prior to, during and after filling. In order to maximize the shelf life of such products, it is crucial that fitment assemblies provide a hermetic seal for the entire life cycle of the container.

One convenient method of dispensing the contents of flexible containers is to open the containers by piercing the cap used to seal the container or by piercing the container directly using a fluid transfer device. Examples of dispensing systems that use piercing are disclosed in the following U.S. Pat. Nos. 4,325,496, 6,378,730 and 7,980,424. A technique generally used in such dispensing systems is force the piercing element through the film of the flexible container. Disadvantages of this technique is that when the piercing element is forced too far into the container, it can pierce the opposite wall of the container and cause a leak and prevent the container from resealing and thereby causing spoilage of the product in the container. Also, if the wall of the container is not pierced, contact with the wall can substantially weaken the wall and later result in a break since often these flexible containers are subjected to stressful handling.

Usually, flexible containers are intended for one-time use and are discarded once the contents of such containers have been completely dispensed; the fitment assembly must be made of inexpensive material, easy to manufacture, quick to market and preferably recyclable. It is also desirable that the fitment assembly for use with such packaging systems simplifies access to the container's contents while also minimizing the potential for contamination of the contents. Preferably, the contents of the flexible containers can also be easily dispensed without tools or the like. It is also desirable that the fitment assembly can be adapted to standard and widely-used spout configurations and can be easily adapted to a flexible hose or tube. The dispensing mechanism must be reliable such that dispensing of the contents is achieved without wasting the liquid through leakage or uncontrolled opening of the connection component and the like.

SUMMARY

The present invention provides a fitment assembly mounted to a flexible container, whereby the wall of the flexible container is pulled into contact with a piercing element and the contents of the container are dispensed by piercing the wall of the container with an assembly having a fluid transfer device.

A piercing fitment assembly for a thin film flexible container containing a liquid comprising:

(A) a spout assembly having a longitudinal through internal passage and a sealing flange sealed to the film of the flexible container and having positioned therein a circular piercing element with a through internal passage and having a circular piercing end with at least one piercing point transversely positioned in the longitudinal passage in close proximity to the film of the flexible container;

(B) a threaded plug having a top and bottom and having a longitudinal through internal passage and a threaded exterior being fitted into the through internal passage of the spout assembly and the bottom of the plug being sealed to the film of the flexible container;

(C) a threaded collar having a longitudinal internal passage and threaded on the interior of the longitudinal passage and positioned in the internal passage of the spout assembly and threadably engaged with the threaded exterior of the threaded plug;

wherein said threaded plug being sealed to the film of the flexible container and positioned in the internal passage of the spout assembly and wherein the circular piercing element and the threaded exterior of the plug being engaged with the threaded interior of the collar; and whereby when engaging the threaded collar to move the threaded plug sealed to the film of the container thereby forcing the threaded plug to move away from the film of the flexible container thereby bringing the piercing end of the piercing element into engagement with the film and thereby piercing the film and allowing the liquid from the flexible container to flow out of the container and through the longitudinal interior of the spout assembly and out of the flexible container.

The piercing fitment assembly is easy to use since a relatively minimal amount of force is required for piercing and establishing fluid transfer. The piercing fitment assembly may be used, for example, with flexible containers that are filled or that are formed and filled using suitable commercial packaging systems known in the art. Such packaging systems may include vertical form film seal filling machines sold under the trade-marks PREPAC, IMPACO and ELECSTER, and, the Liqui-Box™ Filler Model 2000C1T-A that is used for filling flexible containers used in bag-in-box systems. The fitment assembly may also be used with flexible containers that are aseptically filled.

According to one broad aspect, the present invention provides a fluid transfer device for dispensing flowable material from a container by piercing the container. The fluid transfer device comprises a hollow body having: a longitudinal axis, a through internal passage, a piercing end and a dispensing end. The piercing end has a peripheral extremity that is tapered in relation to the longitudinal axis of the hollow body and the piercing end may also have a leading tooth that is located at a distal extrema of the peripheral extremity to initiate piercing of a film secured to the spout of a container.

In another embodiment of the invention, the leading tooth may comprise an exterior surface that is substantially parallel to the longitudinal axis of the hollow body and an interior surface that is inclined inwardly and forms an angle of 10° to 45° with the exterior surface.

Advantageously, the piercing end of the fluid transfer device may further comprise a plurality of additional teeth that are disposed around the peripheral extremity. The additional teeth facilitate piercing as they reduce the amount of force that is required for piercing the film of the flexible container and causing a circular film membrane within the pierceable portion to be peeled back in order to establish fluid transfer.

The piercing end of the fluid transfer device may have a peripheral extremity that is tapered in relation to the longitudinal axis of the fluid transfer device wherein the leading tooth is located at a distal extrema of the tapered peripheral extremity so as to initiate piercing of the film. Advantageously, the piercing end may further comprise additional teeth disposed around the peripheral extremity of the piercing end so as to subsequently and progressively puncture the film during piercing.

According to another aspect, the present invention also provides a flexible container comprising the pierceable port. The pierceable port is secured to the flexible container by a flange secured to the film of the flexible container. The pierceable port may also be secured to the flexible container so that the pierceable portion is aligned with an opening in the flexible container. Alternatively, if the pierceable portion is not aligned with an opening in the flexible container and the flange is secured to an outside wall surface of the container, a portion of the pierceable portion may also be secured to the outside wall surface.

According to yet another aspect, the present invention also provides a piercing fitment assembly for a container comprising a pierceable port and a fluid transfer device. The pierceable port is secured to the film of the flexible container and includes a pierceable portion. The port includes a flange by which it may be secured to the film of the container. The fluid transfer device comprises a through internal passage, to permit fluid communication from the container through the fluid transfer device.

DETAILED DESCRIPTION OF ILLUSTRATIVE EMBODIMENTS

Referring particularly to the drawings, the figures are for the purpose of illustrating the present invention only and not for the purpose of limiting the scope of the appended claims.

Figure 1:
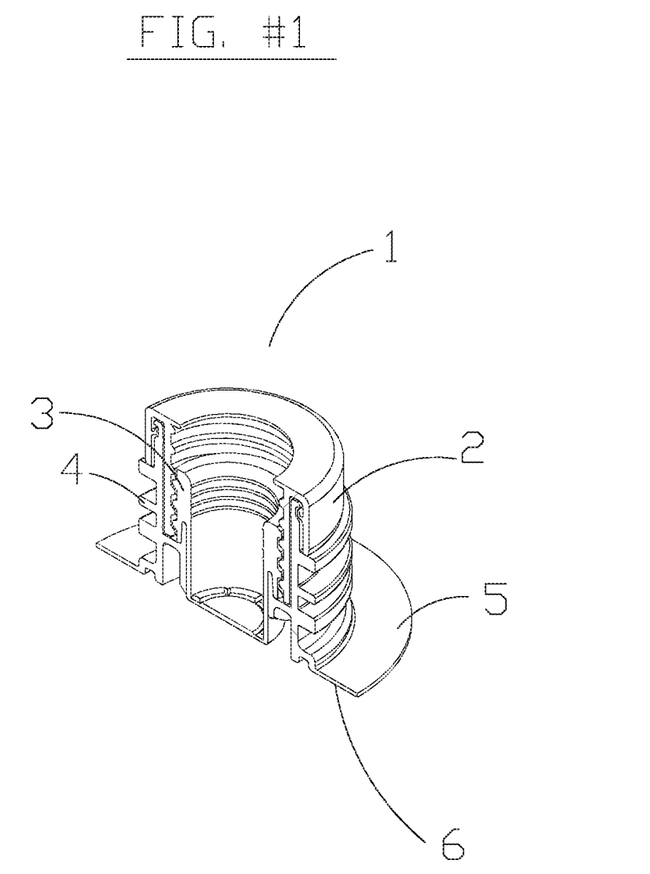
FIG. 1 shows a cross sectional side view of the piercing fitment assembly according to one embodiment of this invention.

FIG. 1 illustrates a piercing fitment assembly shown generally at 1 according to the invention for use with flexible containers for flowable materials, such as liquids or semi-solids, and particularly for aseptically-packaged flexible containers. The piercing fitment assembly 1 comprises a threaded collar 2 having a central opening and is positioned in spout 4 having a generally cylindrical shape and has a through central opening and a flange 5, wherein the bottom 6 of flange 5 is sealed to a bag film, not shown. Hollow threaded plug 3 having external threads is in threaded contact with internal threads of threaded collar 2 and sealed to the bag film (not shown). Sealing to the bag film is accomplished by conventional methods, such as heat sealing, adhesive or the like. A piercing element, not shown in FIG. 1 but is shown in FIG. 2 as piercing element 7, is positioned in the hollow interior of threaded plug 3 and in close relationship to the bag film to readily pierce the bag film when the film contacts the piercing element.

Figure 2:
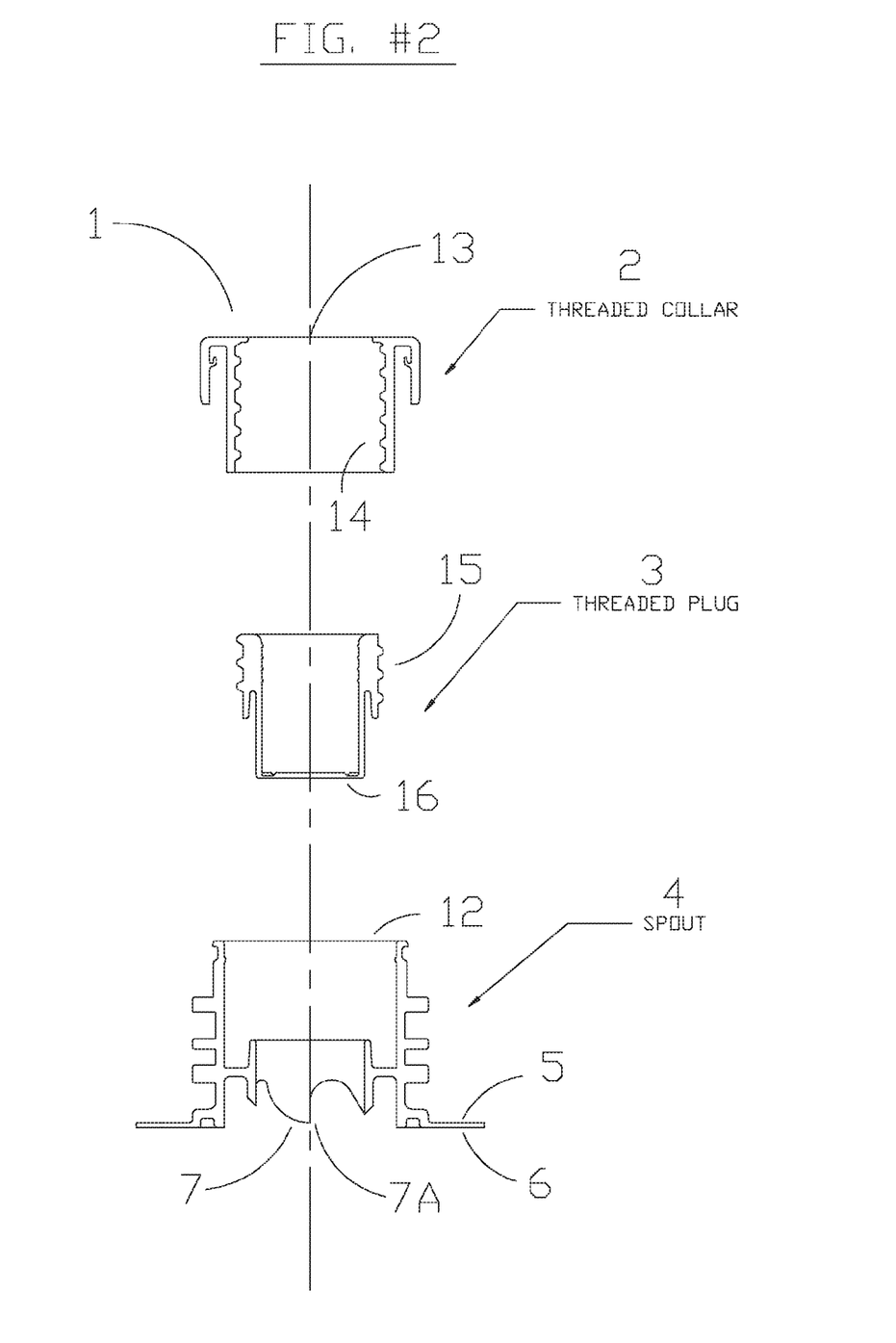
FIG. 2 shows a cross-section side elevation of the piercing fitment assembly in its disassembled state according to one embodiment of this invention.
Figure 2A:
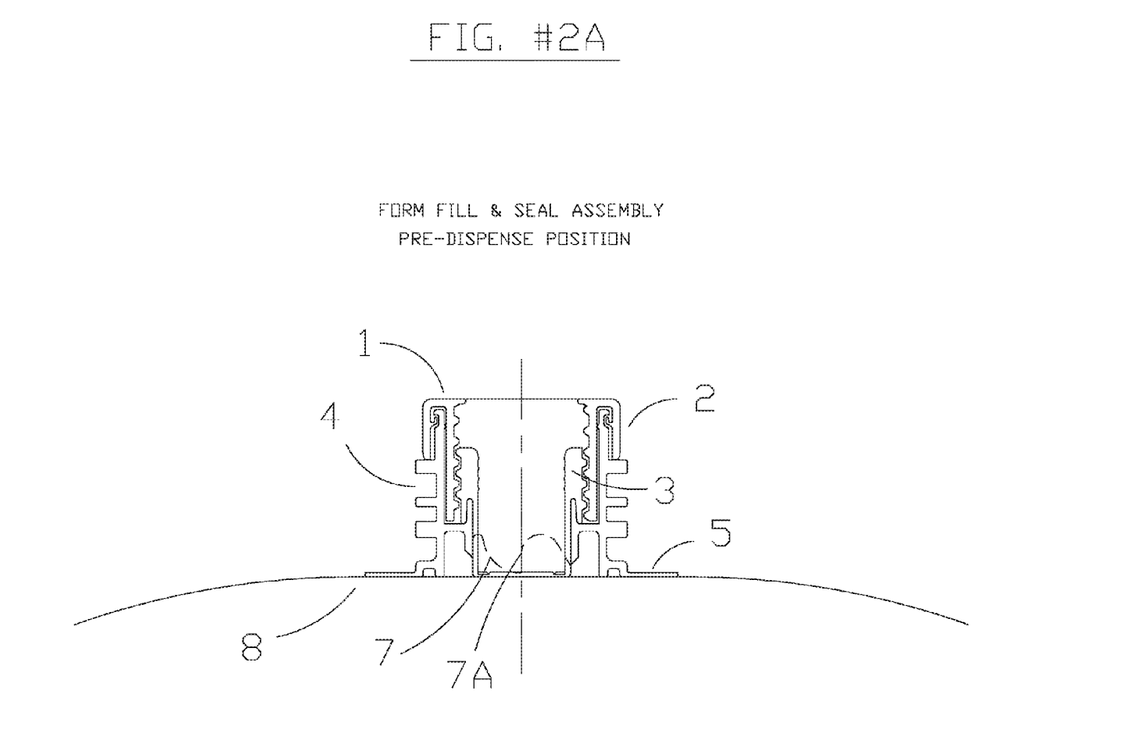
FIG. 2A shows a cross-section of the of the piercing fitment assembly in its pre-dispensing position.

FIG. 2 shows a cross-section side elevation of the piercing fitment assembly 1 in its disassembled state according to one embodiment of this invention. Threaded plug 3 is threaded into the center of threaded collar 2 and the assembly of collar 2 and plug 3 slidably fits into the center opening of spout 4. Flange 5 of spout 4 is sealed to the bag film 8 not shown. As shown in FIG. 2A, a piercing element 7 having a piercing point 7A with a hollow center is mounted in the center of spout 4. The assembly of collar 2 and plug 3 fit within the hollow center of the piercing element 7. Piercing point 7A of the piercing element 7 is in proximate contact with the bag film 8 (not shown).

FIG. 2A shows a cross-section side elevation of the piercing fitment assembly 1 in its assembled state in the pre-dispensing position. Threaded plug 3 is threaded into the center of threaded collar 2 and the assembly of collar 2 and plug 3 slidably fits into the center opening of spout 4 and through the hollow center of piercing element 7 having a piercing point 7A. Piercing point 7A of the piercing element 7 is in proximate contact with the bag film 8. Sealing flange 5 and the bottom of the threaded plug 3 are sealed to the bag film 8. The bag film 8 is held securely in place by sealing flange 5 and the plug 3. In operation of the piercing fitment assembly 1, the threaded collar 2 is turned to move the threaded plug 3 away from the bag film 8. Since the bag film 8 is securely held in place by flange 5 and the plug 3, as the collar is turned and moves away from the bag film 8, the film 8 being attached to the bottom of the threaded plug 3 and flange 5 is held taut and is stretched and forced into contact with the piercing point 7A of the piercing element 7 and is easily punctured as shown in FIG. 2B, allowing liquid to flow out of the bag.

Figure 2B:
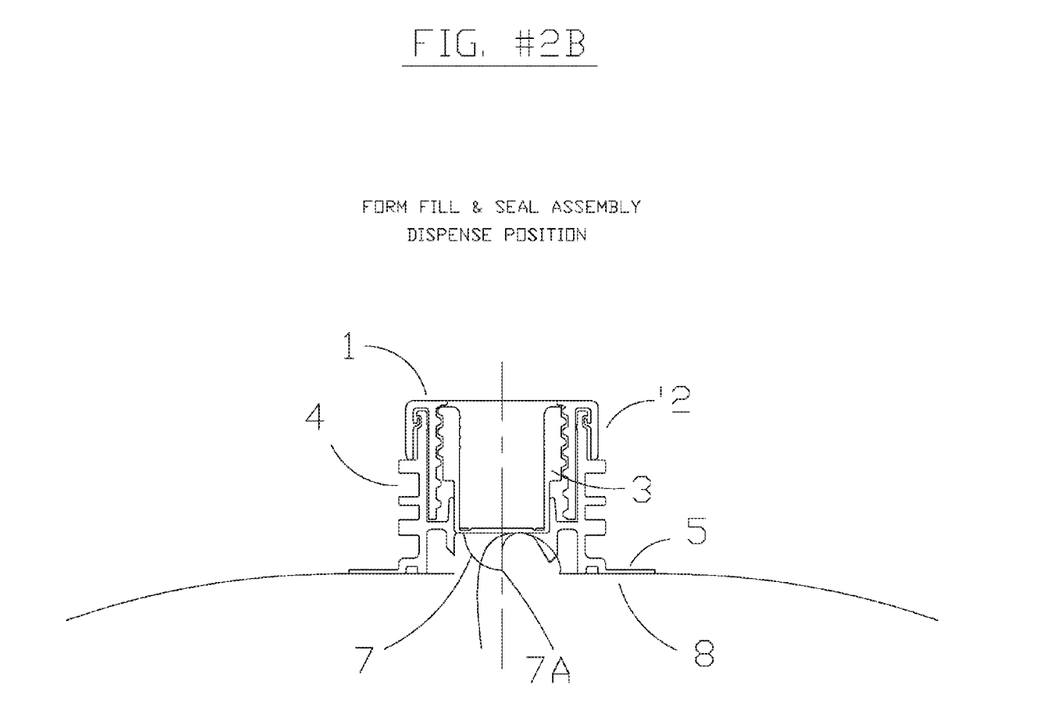
FIG. 2B shows a cross-section of the of the piercing fitment assembly in its dispensing position.

FIG. 2B shows a cross-section of the of the piercing fitment assembly 1 in its dispensing position. The threaded collar 2 has been turned to move the threaded plug 3 attached to the bag film 8 into contact with point 7A of piercing element 7 and the film 8 of the bag has been punctured thereby allowing liquid to flow from the bag.

Figure 3:
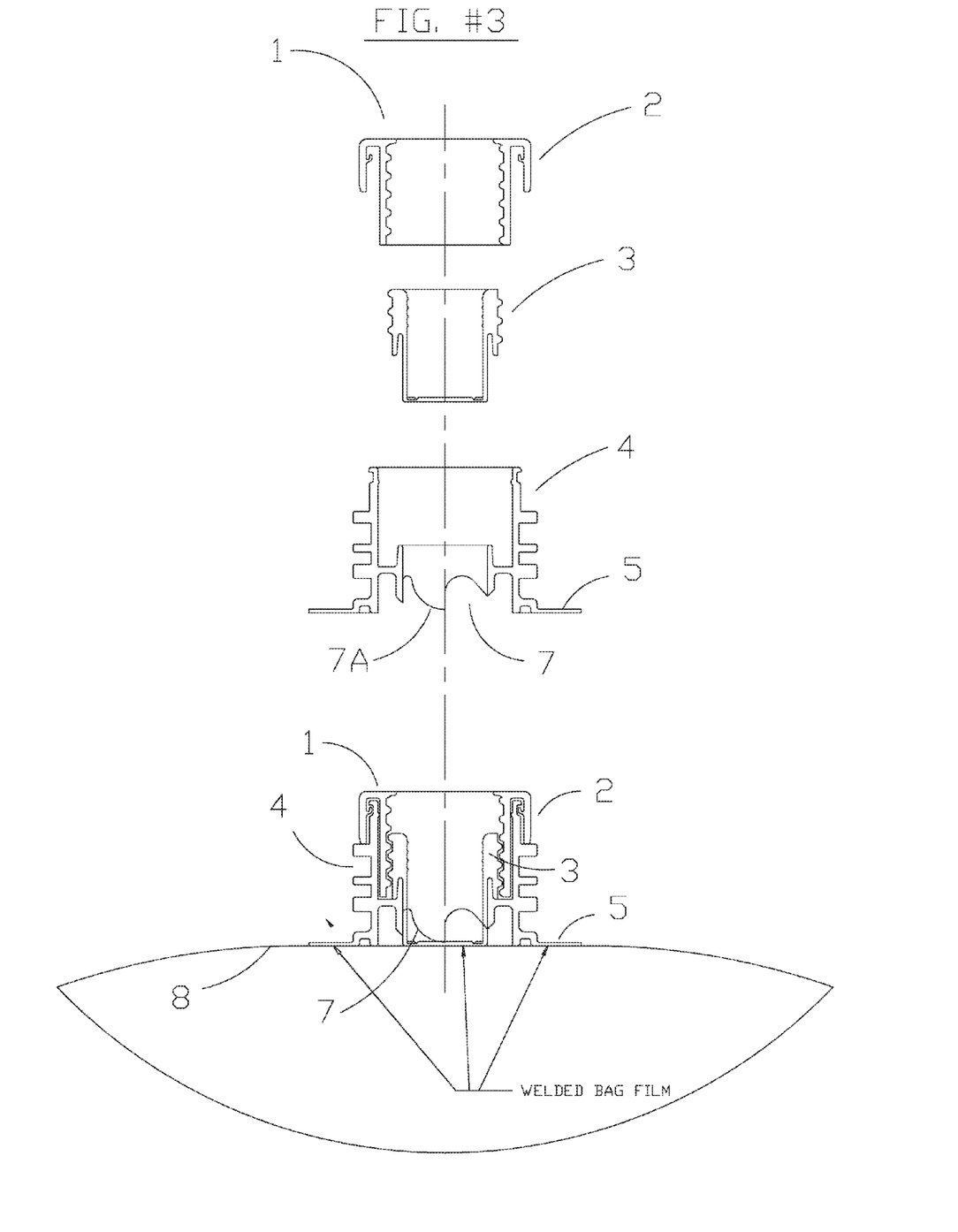
FIG. 3 shows a cross-section side elevation of the piercing fitment assembly in its disassembled state according to one embodiment of this invention and also shows a cross-section side elevation of the piercing fitment assembly in its assembled state according to one embodiment of this invention attached to the bag film of a flexible container.

FIG. 3 shows a cross-section side elevation of the piercing fitment assembly 1 in its disassembled state and also shows a cross-section side elevation of the piercing fitment assembly 1 in its assembled state attached to a bag film 8 and illustrates the piercing element 7 in close relationship to the bag film 8.

Figure 4:
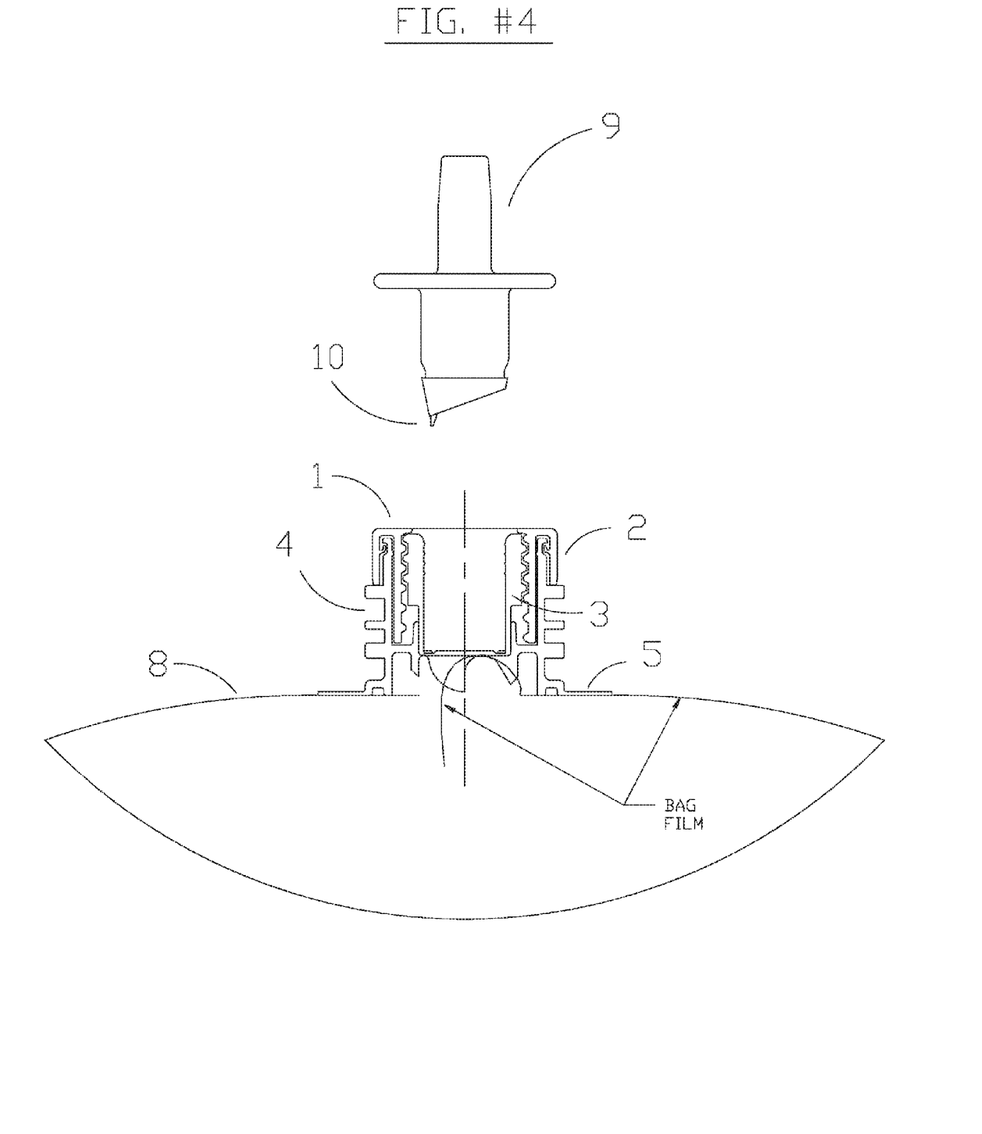
FIG. 4 shows a cross-section side elevation of the piercing fitment assembly in its assembled state attached to a bag film that shows an alternative piercing element 9 having an additional plurality of piercing teeth 10 according to one embodiment of this invention.

FIG. 4 shows a cross-section side elevation of the piercing fitment assembly 1 in its assembled state attached to a bag film 8 that shows an alternative piercing element 9 having an additional plurality of piercing teeth 10 according to one embodiment of this invention. The piercing assembly 1 is sealed to the bag film 8 by flange 5 of the spout 4. The bottom of threaded plug 3, positioned in the spout 4, is sealed to the bag film 8. Threaded collar 2 is threadably engaged with the threaded plug 3 and also positioned in the spout 4. A separate piercing element 9 with piercing teeth 11 is positioned in threaded plug 4. As the threaded collar 2 is turned to move the threaded plug 3 away from the bag film 8, the film 8 sealed to the threaded plug 3 and the flange 5 is forced into contact with the piercing element 7 and the piercing teeth 10 of the piercing element 9 and the bag film is pierced as illustrated allowing liquid to flow from the bag through the piercing fitment assembly.

Figure 5:
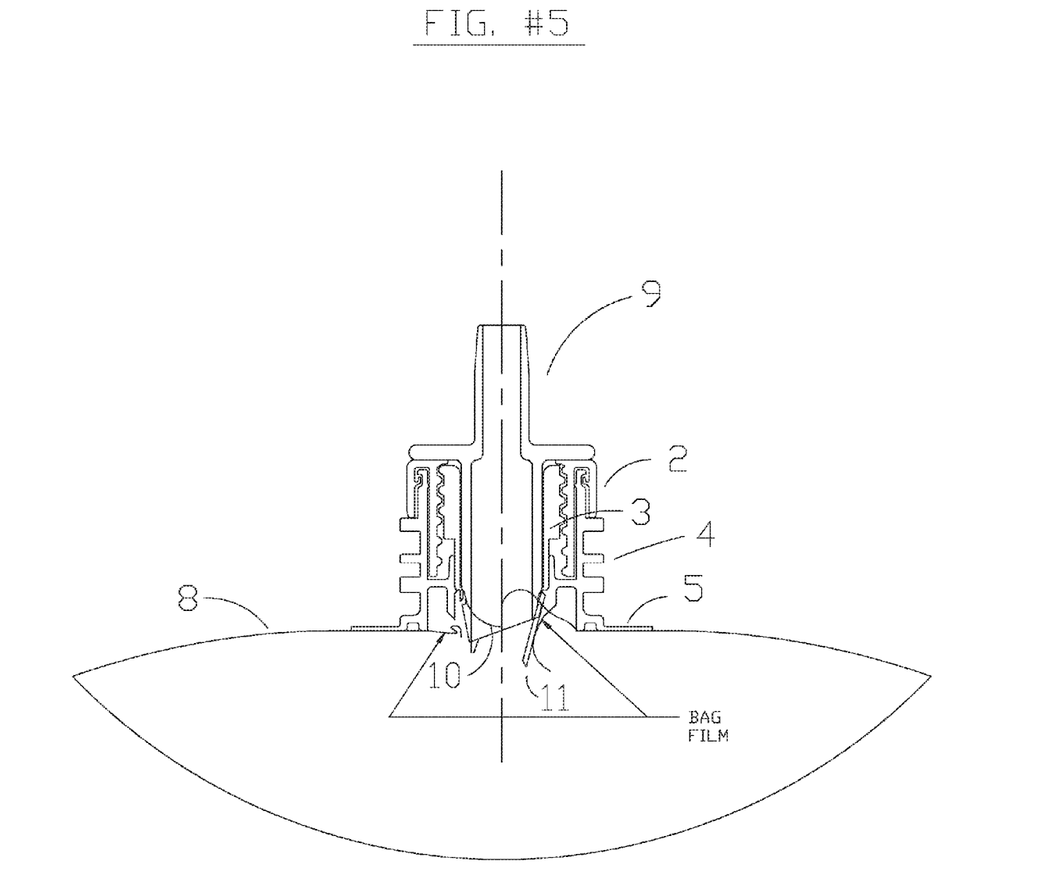
FIG. 5 shows a cross-section side elevation of the piercing fitment assembly in its assembled state attached to a bag film wherein the alternative piercing element has pierced the bag film.

FIG. 5 shows a similar cross-section side elevation of the piercing fitment assembly 1 in its assemble state attached to a bag film 8 showing the alternative piercing element 9 wherein the element has pierced the bag film 8. As in FIG. 4, the piercing element 9 is positioned in the threaded plug 3 in the spout 4. Both flange 5 of the spout 4 and the bottom of threaded plug 3 are sealed to the bag film 8 as in FIG. 4 above. The threaded collar 2 is engaged with the threaded plug 3 and moves the threaded plug 3 away from the film thereby forcing the film into contact with the piercing teeth 10 of the piercing element. The bottom 11 is a flap of film cut by the piercing element that is forced open thereby forming a circular hole in the bag and a flap has been formed.

The configuration of the spout 4 shown in FIGS. 1-5 is widely-used, commercially available and is conventionally adapted for mounting to a flexible bag, typically used "bag-in-box" containers. It is understood that the piercing fitment assembly of the present invention could easily be modified to use other configurations of spouts. The spout 4 has a generally cylindrical shape and has a through central opening 12. The central opening 12 of the spout 4 is in communication with a bag or other type of container (a top portion of a bag is shown, for example, in FIG. 2A). At its base, the spout 4 has a relatively thin outwardly projecting sealing flange 5 that is used to secure the spout 4 to surface of the bag film 8. The bottom surface 6 of the flange 5 of the spout assembly 4 and the bottom of the threaded plug 3 are bonded to form a hermetically seal connection with the outside of the wall of the bag film 8 by known means such as heat sealing, adhesive or the like.

The threaded collar 2 (FIG. 2) has a generally cylindrical shape but could be made to adapt other shapes of spouts such as oval or polygon-shaped and has a central opening 13 that has interior threads 14. The threaded plug 3 having exterior threads 15 is positioned in the central opening 13 of the threaded collar 2 and engaged with the interior threads of the collar 2. The threaded plug 3 is positioned in the central opening 12 of the spout 4 along with the threaded threaded collar 2. The annular edge of the threaded plug 3 is sealed to the bag film 8 of bag container. Positioned in the spout 4 at the annular end of the spout 4 is a piercing element 7 having a hollow interior portion and the threaded plug 3 is positioned therein.

The annular end of the threaded plug 3 is sealed to the bag film 8. The underside 6 of flange 5 of the spout 4 is also sealed to the bag film. The combination of the threaded plug 3 and the flange 5 hold the bag film 8 in a taunt position that allows for only slight movement or distortion of the film. In the operation of the piercing fitment assembly, the threaded collar 2 is turned to move away from the bag or container thereby moving the threaded plug 3 away from the bag or container forcing the film into the piercing element 7 and cutting the film or container. FIG. 3 shows the bag film 8 in contact with the piercing element 7. Further movement of the threaded plug 3 away from the bag film 8 will force the film into cutting contact with the film 8 thereby piercing the film.

FIG. 4 and FIG. 5 each show an alternative piercing element used in place of the piercing element 7 shown, for example, in FIG. 3. The piercing teeth 10 of the alternative piercing element 9 are in close relationship to the bag film 8. U.S. Pat. No. 7,980,424 illustrates such an alternative piercing element and this patent is hereby incorporated by reference. Other designs of piercing elements can also be used.

Filling of flexible containers such as the ones used in bag-in-box systems may be performed on any suitable aseptic filler known to those skilled in the art, and is typically performed using commercial packaging systems such as, for example, the Liqui-Box™ Filler Model 2000C1T-A is not shown. Before filling and aseptic packaging, the container or pouch is supplied to the packaging system in a state where the inside of the container has been pre-sterilized using Cobalt gamma irradiation or any other suitable means of sterilization. The spout 4, threaded plug 3 and the threaded collar 2 are also sterilized using Hydrogen Peroxide (H2O2), steam or any other suitable means. Once the container has been filled with a flowable material, the spout and the threaded plug 3 are hermetically bonded to the film 8. The remainder of the fitment assembly is added and the container is provided to the customer and the container is only opened when the contents of the container are needed.

Since these containers are typically intended for one-time use and are discarded once the contents of such containers have been completely dispensed, it is preferable that the fitment assembly for use in such systems be easy to manufacture, inexpensive, easy to install and use, and recyclable. It is also important that the components are of sufficient quality and robustness. Accordingly, the construction of the components required to produce the piercing fitment assembly of the present invention is relatively simple and economical. The spout 4, threaded collar 2 and threaded plug 3 and any fluid transfer device can all be produced from commonly used and recyclable thermoplastic materials and formed using conventional plastic injection molding processes. For example, the threaded collar and plug may preferably be made using a blend of 85% medium density linear low density polyethylene (LDPE) and 15% high density polyethylene (HDPE). The fluid transfer device may be produced using high density polyethylene (HDPE) or polypropylene (PP). Alternatively, the fluid transfer device may be made using a commercially available low density polyethylene.

Thinner regions of injection molded parts typically impose challenges with respect to suitable mold and process design for injection molding. The specific configuration of such a mold would be apparent to one skilled in the art.

From the foregoing description, it can be seen that the present invention comprises a piercing fitment assembly which is used with flexible containers. It will be appreciated by those skilled in the art that obvious changes can be made to the embodiments described in the foregoing description without departing from the broad inventive concept thereof. It is understood, therefore, that this invention is not limited to the particular embodiments disclosed, but is intended to cover all obvious modifications thereof which are within the scope and the spirit of the invention as defined by the appended claims.

PARTS LIST FOR FIGS. 1-5

1 Piercing Fitment Assembly
2 Threaded collar
3 Threaded plug
4 Spout assembly
5 Sealing Flange of spout
6 bottom surface of flange 5
7 Piercing element
7A Point of piercing element
8 Bag film
9 Separate piercing element
10 Piercing teeth of separate piercing element
11 Flap of threaded plug
12 Central opening of spout 4
13 Central opening of threaded collar
14 Interior threads of collar 2
15 Threaded exterior of threaded plug 3
16 Annual edge of threaded plug 3

What is claimed:

1. A piercing fitment assembly for a thin film flexible container containing a liquid comprising:
  (A) a spout assembly having a longitudinal through internal passage and a sealing flange sealed to the thin film of the flexible container and having positioned therein a circular piercing element with a through internal passage and having a circular piercing end with at least one piercing point transversely positioned in the longitudinal through internal passage of the spout assembly in close proximity to the thin film of the flexible container;
  (B) a threaded plug having a top and a bottom and having a longitudinal through internal passage and a threaded exterior being fitted into the longitudinal through internal passage of the spout assembly and the bottom of the plug being sealed to the thin film of the flexible container;
  (C) a threaded collar having a longitudinal internal passage and threaded on the spout assembly and positioned in an interior of the longitudinal through internal passage of the spout assembly and threadably engaged with the threaded exterior of the threaded plug;
  wherein said threaded plug being sealed to the thin film of the flexible container and positioned in the longitudinal through internal passage of the spout assembly and wherein the circular piercing element and the threaded exterior of the threaded plug being engaged with the interior of the threaded collar; and
  whereby when engaging the threaded collar to move the threaded plug sealed to the thin film of the flexible container thereby forcing the threaded plug having the thin film sealed thereto to move away from the thin film of the flexible container thereby bringing the piercing end of the piercing element into engagement with the thin film and thereby piercing the thin film and allowing the liquid from the flexible container to flow out of the flexible container and through the longitudinal through interior passage of the spout assembly and out of the flexible container.

2. The fitment assembly of claim 1 wherein the piercing element comprises a circular blade having at least one sharp piercing point.

3. The fitment assembly of claim 1 wherein a separate piercing element is positioned in the spout assembly.

4. The fitment assembly of claim 3 wherein the separate piercing element comprises circular hollow body having piercing tooth with an interior surface and an exterior surface that is substantially parallel to a longitudinal axis of the circular hollow body; the interior surface is inclined inward at an angle of 1-90° with the exterior surface.

5. The fitment assembly of claim 3 wherein the separate piercing element comprises circular hollow body having piercing tooth; each tooth having an interior surface and an exterior surface that is substantially parallel to a longitudinal axis of the circular hollow body; the interior surface is inclined inward at an angle of 10-45° with the exterior surface.

6. The fitment assembly of claim 1 wherein the threaded collar further comprises a fluid transfer device.

7. A thin film flexible container comprising the fitment assembly of claim 1 attached thereto.

8. The thin film flexible container of claim 7 comprising an aseptically packaged flexible container.

* * * * *

UNITED STATES PATENT AND TRADEMARK OFFICE
CERTIFICATE OF CORRECTION

Page 1 of 1

PATENT NO. : 9,862,531 B2
APPLICATION NO. : 15/002577
DATED : January 9, 2018
INVENTOR(S) : James W. Johnson It is certified that error appears in the above-identified patent and that said Letters Patent is hereby corrected as shown below:

In the Specification

Column 4,
Line 4, delete "of the" (second occurrence).
Line 6, delete "of the" (second occurrence).

Signed and Sealed this
Eighth Day of January, 2019

Andrei Iancu
*Director of the United States Patent and Trademark Office*